United States Patent [19]

Goering et al.

[11] Patent Number: 5,013,561

[45] Date of Patent: May 7, 1991

[54] PROCESS FOR RECOVERY OF PRODUCTS FROM WAXY BARLEY

[75] Inventors: Kenneth J. Goering; Robert F. Eslick, both of Bozeman, Mont.

[73] Assignee: Barco, Inc., Bozeman, Mont.

[21] Appl. No.: 287,663

[22] Filed: Dec. 20, 1988

Related U.S. Application Data

[63] Continuation-in-part of Ser. No. 150,434, Jan. 28, 1988, Pat. No. 4,804,545, which is a continuation of Ser. No. 914,877, Oct. 3, 1986, abandoned, which is a continuation of Ser. No. 639,345, Aug. 10, 1984, abandoned.

[51] Int. Cl.$^5$ .......................... A23L 1/10; A23J 1/12; C12P 19/22; C12P 19/14
[52] U.S. Cl. .......................... 426/28; 426/44; 426/52; 426/430; 426/436; 435/95; 435/99
[58] Field of Search ............... 426/11, 28, 29, 44, 426/52, 430, 436; 435/99 95

[56] References Cited

U.S. PATENT DOCUMENTS

| | | | |
|---|---|---|---|
| 1,548,721 | 8/1925 | Ling et al. | 426/28 |
| 3,576,645 | 4/1971 | Rozsa | 99/31 |
| 3,689,277 | 9/1972 | Sfat et al. | 99/28 |
| 3,791,865 | 2/1974 | Hurst et al. | 127/32 |
| 3,846,397 | 11/1974 | Ernster | 260/112 R |
| 3,901,725 | 8/1975 | Bond et al. | 127/33 |
| 4,042,414 | 8/1977 | Goering et al. | 127/32 |
| 4,069,103 | 1/1978 | Muller | 195/4 |
| 4,116,770 | 9/1978 | Goering et al. | 195/63 |
| 4,311,714 | 1/1982 | Goering et al. | 426/28 |
| 4,428,967 | 1/1984 | Goering et al. | 426/28 |
| 4,448,790 | 5/1984 | Sarkki et al. | 426/52 |
| 4,804,545 | 2/1989 | Goering et al. | 426/28 |

*Primary Examiner*—David M. Naff
*Attorney, Agent, or Firm*—Lowe, Price, Leblanc, Becker & Shur

[57] ABSTRACT

Waxy barley grain is processed by a series of processing steps to produce beta-glucan solids, a bran residue, a protein concentrate, barley oil and a maltose syrup in uncontaminated form. The process involves steps of mixing a meal produced from waxy barley grain with water, separating barley solids and a water extract, heating the water extract and separating coagulated protein and beta-glucan solids, mixing the barley solids with water and separating a bran fraction and crude starch, forming a dough from the crude starch and separating gluten and waxy barley starch from the dough, mixing the bran fraction with water and enzymes to carry out starch conversion and produce a liquid mixture, separating solids from the liquid mixture, extracting the solids with alcohol to produce oil and recovering maltose syrup from liquid remaining after separating the solids.

21 Claims, 1 Drawing Sheet

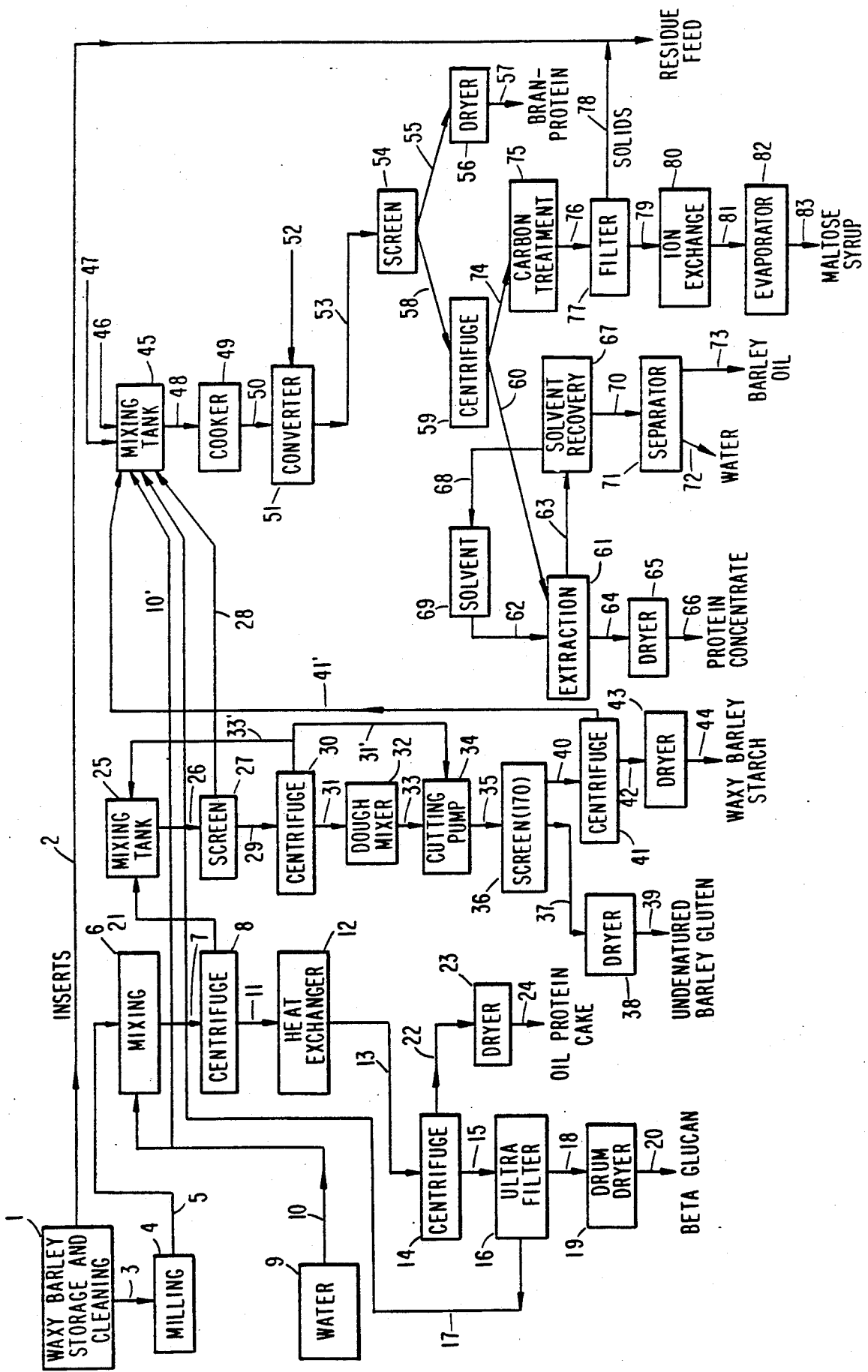

PROCESS FOR RECOVERY OF PRODUCTS FROM WAXY BARLEY

This is a continuation-in-part application of U.S. application Ser. No. 150,434 filed on Jan. 28, 1988, now U.S. Pat. No. 4,804,545 which is a continuation of U.S. application Ser. No. 914,877 filed on Oct. 3, 1986, now abandoned, which is a continuation of U.S. application Ser. No. 639,345 filed on Aug. 10, 1984, now abandoned, all by the same inventors.

TECHNICAL FIELD

This invention relates to the improved processing of waxy barley grain to obtain valuable products therefrom. More particularly, this invention relates to the processing of waxy barley grain for the production of a maltose syrup, beta-glucans, a barley oil, and protein bran products.

BACKAGROUND ART

Barley is a grain product useful, e.g., in the brewing industry as barley malt. The enzymatic activity of the barley malt is utilized for industrial applications such as starch-splitting and protein degrading. Barley malt is an important source of alpha- and beta-amylase, and is used in many foods, such as beer, wheat flour and cereal to convert starch to fermentable sugars.

Very limited work has been conducted relating to the utilization of barley in other areas. Exemplary prior art attempts to use barley in other ways may be found primarily in U.S. Pat. Nos. 4,311,714 and 4,428,967 and U.S. Pat. No. 4,804,545 by the present inventor. In these patents and the prior application, novel procedures are set forth for the production and recovery of maltose syrup, protein products, barley oil, bran and a carbohydrate gum. The present method is an improvement on these prior processes.

U.S. Pat. No. 4,804,545 referred to above discloses a method for producing and recovering beta-glucan solids, bran residue, a protein concentrate, barley oil and maltose syrup from waxy barley, comprising (1) reducing the particle size of the waxy barley to form a meal, heating the meal at 90°-115° C. to effect inactivation of natural enzymes in the meal and form an enzyme-inactivated meal, extracting beta-glucan solids from the enzyme-inactivated meal by mixing the meal solely with water at 40°-60° C. and producing a water extract and barley solids, and recovering the beta-glucan solids from the water extract, (2) recovering the barley solids, mixing with water, and adding an amylolytic enzyme and a beta-glucanase enzyme, heating at 70°-75° C. to effect starch conversion, (3) cooling to 50°-60° C. and adding an enzyme which has alpha-amylase activity and maintaining the mixture at this temperature to complete starch conversion and form a starch mixture, (4) separating rough solids from this starch mixture and recovering a bran residue rough solids, (5) separating solids from the liquid in the remaining starch mixture, separating solids from the liquid, extracting the solids with an alcohol to recover a protein concentrate and an extracted barley oil, (6) recovering the barley oil and protein concentrate, and (7) recovering maltose syrup from the liquid of step (5).

In addition, U.S. Pat. No. 3,846,397 processes grain residues obtained from mashed barley malt to recover water soluble protein products suitable for utilization as animal feeds. U.S. Pat. No. 1,548,721 describes the treatment of starch with an ungerminated grain such as barley until the major portion of the starch has been saccharified. U.S. Pat. No. 3,689,277 discloses production of a protein hydrolysate from barley grain by treating with a proteolytic enzyme at 35°-50° C. to produce protein hydrolysis products and a starch fraction, the solution containing at least 40% of protein. The protein is then reacted with sugar to produce a product having a caramel flavor.

U.S. Pat. No. 3,901,725 describes wet processes for separating cereal starch granules according to size and states that barley, rye and wheat starch may be treated in the process. However, this patent does not set forth specific examples of obtaining any product from a barley grain. U.S. Pat. No. 4,094,700 is directed to a method for producing gluten and starch from a dispersion of wheat, barley or rye endosperm fractions in water. However, there is no actual example directed to processing of barley as the starting material or any description of a product obtained from barley.

A publication entitled "Barley Syrup Production" by The ABMIP/DDS-KROYER Process, Pamphlet No. 815G008E, published by the Danish Company, DDS-KROYER, presented in 1972 in Peking by Erik S. Nilsson, discloses a conventional procedure for processing of barley by conversion to malt through germination of the raw barley. A process is disclosed wherein an extract simulating the extract from barley malt action can be produced by degrading barley directly with enzymes such as alpha-amylase or beta-amylase.

U.S. Pat. No. 3,791,865 discloses maltose syrups obtained from corn starch wherein the syrup contains 60-80% maltose and 15-35% maltotriose.

Most of the prior art processes are complex, time consuming, involve several steps, require high energy input and result in products substantially contaminated with one another.

Accordingly, there is still a need for an improved method of preparing beta glucan solids, a bran residue, a protein concentrate, barley oil and a maltose syrup from waxy barley which produces highly uncontaminated products and is fast and simple to practice.

DISCLOSURE OF THE INVENTION

The present invention provides a series of processing steps by which several valuable products are obtained from waxy barley.

The present invention provides a method for processing waxy barley grain to produce a high maltose carbohydrate syrup, a protein-concentrate, a barley oil, a carbohydrate gum, barley starch and bran-protein.

The invention described herein provides a novel and improved process by which these products can be obtained utilizing a continuous procedure whereby the products are obtained in highly pure form so that they may be used, e.g., in a wide spectrum of food industry products.

This invention relates to a continuous manufacturing process for the recovery of various products from waxy barley starting materials or grain, comprising a barley syrup, a barley oil, a protein concentrate, beta-glucan solids, a barley starch and bran protein residue, among others. The manufacturing method of this invention comprises treatment of waxy barley grain, e.g, a barley grain containing at least about 92 wt % amylopectin, in accordance with the novel method of the invention.

The present is a method for producing and recovering beta-glucan solids bran residue, a protein concentrate, barley oil waxy barley starch and maltose syrup from waxy barley, comprising (a) reducing the particle size of the waxy barley to form a meal;

(b) mixing the meal solely with water at a temperature of about 40°-60° C. to produce a water extract and barley solids;

(c) separating barley solids from the water extract, heating said water extract at about 80°-115° C., separating coagulated protein from the extract and separating beta-glucan solids containing less than about 5 wt % protein from the remaining water extract;

(d) mixing the barley solids with water, adding an amylolytic enzyme and a beta-glucanase enzyme, heating at a temperature of about 70°-75° C. for sufficient period to effect starch conversion;

(e) cooling the mixture to about 50°-60° C. and adding an enzyme which has at least alpha-amylase activity and maintaining the mixture at this temperature to complete starch conversion and form a starch mixture;

(f) separating rough solids from the starch mixture and recovering a bran residue rough solids;

(g) separating solids from the liquid in the remaining starch mixture, extracting the solids with an alcohol to separate a protein concentrate and an extracted barley oil, and separately recovering the barley oil and the protein concentrate; and (h) recovering maltose syrup from the liquid of step (g).

This invention also relates to a waxy barley composition comprising a waxy barley starch substantially free of beta-glucans obtained by the method of this invention.

Also part of this invention is a barley oil composition comprising a barley oil obtained by the method of the invention.

Also provided herein is a beta-glucans composition containing less than 5 wt % protein comprising a beta-glucan solids preparation obtained by the method of this invention.

Still part of this invention is a bran composition comprising a bran residue rough solids preparation obtained by the method described above.

Still another part of the invention is a protein concentrate composition comprising a protein concentrate product obtained by the method described above.

And also provided herein is a maltose composition comprising a maltose syrup obtained by the method of this invention.

A more complete appreciation of the invention and many of the attendant advantages thereof will be readily perceived as the same becomes better understood by reference to the following detailed description when considered in connection with the accompanying figures.

BRIEF DESCRIPTION OF THE DRAWING

The FIGURE is a schematic flow sheet for a commercial processing system in accordance with the process of the present invention.

Other objects and advantages of the present invention will become apparent as the description thereof proceeds.

DESCRIPTION OF THE PREFERRED EMBODIMENTS

This invention arose from a desire to improve on prior methods by the present inventor useful for the preparation of beta-glucan solids, a bran residue, a protein concentrate, barley oil, barley starch and a maltose syrup, among others.

The present invention is concerned with the preparation of a number of novel products from waxy barley grain. These products are useful, e.g., in various industrial applications. In particular the method of the invention produces a maltose syrup, a protein concentrate, a bran-protein product, a barley starch substantially free of beta-glucans and a low-protein beta-glucan product, among others.

The method of the invention may be practiced utilizing waxy barley substrates of various strains which are known in the art. The waxy barleys are chemically similar to starch found in corn waxy varieties but the physical properties of the waxy barley starch are different from those of ordinary corn starch. These properties make the barley starch easier and less expensive to process as well as more desireable for certain applications (Wu et al, "Preparation and Evaluation of Doubly Modified Waxy Barley Starch", 692 No. 2031, Vol. 33(8) (August 1988)), the entire content thereof being incorporated herein by reference to show types of starches made from waxy barley and their superior characteristics over maize starches.

Several waxy barleys are described in the prior art, for example in the inventors' publications in Cereal Chemistry, 53 (2) pages 174-180, (1975), and Cereal Chemistry, 55, (2), pages 127-137, (1977), as well as their prior U.S. Pat. Nos. 4,042,414, issued Aug. 16, 1977, 4,054,671, issued Oct. 18, 1977 and 4,116,770, issued Sept. 26, 1978. These waxy barleys are produced by cross-breeding barley varieties having different genes as described in these publications. These publications and prior patents describe a barley species which is self-liquefying (Washonupana) and other waxy barleys (Wapana and Waxy Oderbrucker). The entire contents of the disclosures of the above publications are hereby incorporated by reference, particularly the disclosures which compare waxy barleys with normal barleys.

Other species of waxy barleys which may be used as starting materials in the process of the invention include Watan, Wabet, Washonutan, Washonubet, Wanutan, Wanubet, and Wanupana. It should be noted that waxy barleys are usually named with the prefix "wa-", and normally contain about 98-99 wt. % of amylopectin. It should be understood that the waxy barley starting material is not limited to those named herein and may be variously derivatized.

In addition, other equivalent starting materials may also be employed providing that they are waxy type products which contain less than about 8% amylose, or alternatively at least about 92 wt % amylopectin. It should be noted that a normal barley contains about 72-80 wt % amylopectin. A difference, inter alia, between waxy barley and normal barley being the amylopectin content.

The novel method of the present invention produces several major products from the waxy barley starting material through a series of processing steps. These products may be broadly described as a beta-glucan product, a bran-protein product, a syrup containing in excess of about 50% maltose, and generally in the range of about 52%-60% maltose by weight, a protein concentrate, a barley starch and a barley oil, among others. Alternate products can also be produced. The maltose syrup concentrate may further be catalytically reduced to produce malitol which is a commercial sweetener and is considered as an optional product to be produced from the barley in addition to those named above. Thus, this invention provides a large number of potential commercially useful products which can be recovered from the barley grain in accordance with the present method. In view of the limited use of barley heretofore, this represents an outstanding contribution to the art of processing barley grain.

Of the several products produced, the bran-protein is useful as a food supplement, particularly with current emphasis on the addition of fiber to the diet. Products low in protein content could be used as animal feeds whereas high protein containing materials such as the protein concentrate are useful as a substitute for vital gluten which is obtained from wheat. The maltose syrup and the high protein products obtained from the barley according to the present invention are commercially attractive products having novel physical and chemical characteristics. Barley protein products are also useful for incorporation into the diets of people who are allergic to wheat protein.

The maltose syrup comprises in excess of about 60 wt % maltose and less than about 5 wt % dextrose and with proper concentration, contains up to about 80 wt % solids. Thus, this type of product is highly desirable and is useful in bakery and dairy products such as cereal, sweeteners, ice cream, and brewing operations as well as hard candy products. For example, in the ice cream industry, the maltose syrup is useful in providing texture for body and crystallinity control.

These products are produced by a multi-step method comprising the processing of barley grain. This process is described in general in the accompanying drawing, which is set forth as a flow chart. The present invention represents an improvement in processing of these materials over the methods described in prior U.S. Pat. Nos. 4,311,714 and 4,428,967, and U.S. application Ser. No. 150,434 filed on Jan. 28, 1988, all by the present inventors.

The improvements taught by the novel method described herein include the removal of substantially all the beta-glucan prior to starch conversion, thus permitting an extraction of the water soluble beta-glucans in substantial amounts, for example, up to about 4-7 wt % prior to starch conversion. This results in substantially improved yields of beta-glucans to yield a potentially valuable by-product and at the same time improve the syrup conversion factor since most of the beta-glucan is eliminated from the processing meal. With the substantial removal of the beta-glucans, it is found that the wet milling step can be eliminated and the finely milled grain mash can be directly converted without the separation of crude starch. As a result, these two operations are eliminated. These modifications greatly improve the efficiency of the method of the invention as well as the purity of the resulting products. This operation also eliminates the problem of processing mill water since that fraction is also eliminated.

In addition, the present method no longer requires heating the barley meal to attain enzyme inactivation prior to the separation of the beta-glucans. In the present method, after reduced particle waxy barley is provided as a meal, it is mixed solely with water at a temperature of about 40° to 60° C. to produce a water extract and barley solids. Thereafter, the barley solids are separated from the water extract and the water extract is heated at about 80° to 115° C. and then the beta-glucan solids containing less than about 5 wt % protein, and in some instances less than about 3 to 4 wt % protein, are separated. The beta-glucans are separated at a temperature of about 80° to 115° C., and more preferably about 90° to 95° C. without significant degradation of the beta-glucans by native beta-glucanase. The entire step takes in general less than about 15 minutes, and in some instances less than about 10 minutes, and more preferably less than about 5 minutes. Typically, this step may be conducted for a period of time of about 30 seconds to 5 minutes or longer as seen appropriate. Thereafter coagulated protein is separated from the water extract and then the beta-glucan solids are further separated from the remaining water extract. This step yields roughly in excess of about 3% of an oil-protein coagulated product and reduces the protein content of the beta-glucan solids from about 20-25 wt %, in many instances to less than about 5 wt % protein, and in some instances less than about 3 to 4 wt %. The oil-protein coagulated solids roughly contain about 50 wt % protein and about 6 wt % oil. However, different proportions may also be obtained depending upon the type of barley substrate utilized and/or the conditions used for the various steps.

Thus, the present invention provides a procedure by which the products produced by this invention, namely the maltose syrup, the bran protein residue, the beta-glucans, a 75-80% protein concentrate and barley oil, are produced from barley grain by a multi-step procedure. As described in the flow sheet accompanying the application, the waxy barley is initially obtained from storage and cleaned to remove inert particles, dirt and the like. The inerts and other impurities may be mixed with a filter cake residue for disposal or use as desired and are removed through line 2. The grain is then removed by line 3 and milled in a conventional grinding apparatus such as a hammer mill 4. During milling, it is desirable to grind the grain to a point wherein all of the material will pass through an about 45 mesh screen, but this may be varied. The resulting milled product is then passed by line 5 to a mixing tank 6, where the ground grain is mixed with 5 to 7 parts of water, preferably about six parts of water, from source 9 through lines 10 and 10'. The water is preferably preheated so that it is at a temperature of about 40°-60° C., preferably about 55° C., for mixing with the grain at this stage. The grain and water mixture should remain in the mixing tank 6 for about 1-2 minutes to achieve thorough mixing of the grain with the water. The tank is preferably provided with a high speed agitator to accelerate the mixing procedure.

On completion of mixing, the resulting product is removed by line 7 to a decanter centrifuge 8 to effect a separation between the rough solids and the liquids. The centrifuge may be any conventional device of this type which will remove most of the solids, such as a decanter centrifuge. If a decanter is used, the liquids should be subjected to a desludging step to remove sludges therefrom. Any sludges removed may then be mixed with the solids from the decanter. These solids are transferred by line 21 to the mixing tank 25. The liquids are removed from the centrifuge by line 11 to a heat exchanger 12 where they are instantaneously heated to about 80° to 115° C. to sterilize the system to inactivate the remaining enzymes and to coagulate soluble protein. The liquid from heat exchanger 12 passes the line 13 to centrifuge 14 where the solids are transferred by line 22 to dryer 23. The dried material 24 is oil-protein cake. The liquids from the centrifuge 14 are removed by line 15 to reactor 16 wherein a ultrafiltration procedure is carried out to remove the soluble sugars and concentrate the solution which contains the beta-glucan solids. The water removed in the ultrafiltration apparatus is recycled by line 17 to mixing tank 45 as make up water. The concentrate from the ultrafiltration apparatus 16 are removed by line 18 for drying, preferably in drum dryer 19. The beta-glucan solids are then recovered at line 20 as a final product.

The solids from centrifuge 8 which comprise meal solids are removed by line 21 to mixing tank 25 where they are mixed with water from line 10. Sufficient water is added to obtain a mixture containing from about 20-30% dry solids. The water is also preferably maintained at a temperature of about 50°-55° C. in this portion of the process.

This tank is also equipped with a high speed mixer. This slurry is passed by line 26 to an about 120 mesh screen 27. The retained solids are transferred by line 28 to mixing tank 45. The liquid passing through the screen is transferred by line 29 to centrifuge 30 where the solids are removed and are transferred by line 31 to dough mixer 32. Part of the liquid from centrifuge 30 is recycled via line 33 to mixing tank 25 thus reducing the amount of makeup water in the mixing tank. The solids in the dough mixer are kneaded to make a heavy dough which is transferred by line 33 to cutting pump 34 where additional liquid from centrifuge 30 is transferred by line 33 to cutting pump 34.

The slurry from the cutting pump passes by line 35 to screen 36. The retained solids from screen 36 pass by line 37 to dryer 38 which produces undenatured vital barley gluten 39. The material passing through the screen 36 is transferred by line 40 to centrifuge 41 which separates the purified starch. The starch is transferred by line 42 to dryer 43 producing waxy barley starch 44. The light phase from centrifuge 41 is transferred by line 41' into mixing tank 45 where it is used as makeup water for the syrup process.

At this point, there are preferably added two different kinds of enzyme through lines 46 and 47. One of the enzymes is a beta-glucanase preparation produced by fermentation which will hydrolyze any beta-glucans remaining therein. There is also added an alpha-amylase containing preparation to furnish amylases for conversion of the thin starch to sugars. The beta-glucanase enzyme is preferably a commercial product sold as Cereflo, e.g. Cereflo 200L. The amylase enzyme is preferably the commercial product, Wallerstein's Malt Enzyme PF, available from the Wallerstein Company. Preferably, however, an enzyme which will provide both the alpha- amylase function and beta-amylase functions is used. Green malt enzymes are preferably suitable for this purpose. Preferably, about 0.01 to 1% by weight of the enzymes are added, preferably about 0.5% of the green malt enzyme.

After addition of the enzymes, the mixing is continued in mixing tank 45 to achieve intimate association of the enzymes with the meal solids. In general, about $\frac{1}{4}$ to 1 hour is sufficient for this purpose. Thereafter, the resulting mixture is transferred by line 48 to a cooker 49 where the contents are heated in the range of 70°-75° C. and held at that point for about 1 minute to 10 minutes, preferably 1 minute to 5 minutes, to begin the starch conversion. The resulting cooked grain mash is then transferred by line 50 to converter 51 and cooled to about 55°-65° C., preferably about 60° C. and maintained at this temperature while an additional amylolytic enzyme such as the about 0.5% green malt is added through line 52. This green malt preferably has both alpha-amylase and beta-amylase activity. A beta-glucanase enzyme, (e.g., 10 ml per 100 pounds dry solids) may also be added at this stage to hydrolyze any beta-glucans carried over. The resulting mixture is then maintained at this temperature for about 4 to 8 hours to complete the conversion.

On completion of the starch conversion, the contents of the converter 51 are removed by line 53 to a solid or screen separator such as a Rotex Screen 54, where the solids are retained on a screen. Preferably about a 120 mesh screen is used. The solids are then removed by line 55, and dried in dryer 56. There is recovered from the dryer at line 57 a bran protein residue which is a high protein high fiber product with a pleasant flavor and is ideal as a food supplement.

In the meantime, the liquid from the screen separator 54 is recovered in line 58 and passed through centrifuge 59. Any sludges in the liquids may be removed in a desludging operation. This centrifuge is preferably a disc centrifuge or ultra centrifuge which will effect a further separation of solids and liquids to provide solids which may be removed by line 60. The solids in line 60 are then passed to an extraction device where they are mixed with a lower alkyl alcohol, preferably ethyl alcohol and more preferably, 95% ethyl alcohol from line 62. In the extractor 61, the alcohol extracts barley oil from the solids and these are removed by line 63 as a solution. The resulting solids from the extractor 61 are removed by line 64 and dried in dryer 65 to provide a protein concentrate from line 66. This protein concentrate contains about 75-80% protein.

The liquid phase in line 63 from the extractor 61 is first subjected to alcohol recovery as in distillation recovery column 67. The alcohol recovered is passed by line 68 to alcohol storage 69. The residue after removal of the alcohol is removed by line 70 to separator 71 where water is removed at 72 to provide a barley oil at 73.

The liquid from the centrifuge 59 is removed by line 74 for purification. Preferably, the liquid is initially subjected to a carbon treatment at 75 to decolorize the liquid using a conventional carbon absorption system. The resulting product is then removed by line 76 to filter 77 where any carbon particles and inert materials are removed by line 78. The filtered liquid is then transferred by line 79 and subjected to an ion exchange procedure in ion exchange column 80 to deionize the liquid and effect further purification. The resulting liquid is removed by line 81 and evaporated in a conventional evaporator 82 to produce in line 83 a maltose syrup which contains about 80% maltose solids.

It will be understood, therefore, that the invention provides methods by which the beta-glucan is removed prior to starch conversion with substantial increases in yield. This also enables the elimination of steps which are not economic.

The following example is presented to illustrate the invention, but it is not to be considered as limiting thereto. In the example, and throughout the specification, parts are by weight unless otherwise indicated.

EXAMPLE I

Method in Accordance With the Invention

This example was conducted utilizing substantially similar conditions as in the examples of U.S. Pat. No. 4,804,545, except for the improvements comprised by the present invention. Therefore, a direct comparison of the results obtained by practicing both methods can be made, which shows the unexpected superiority of the present method.

This example describes a run made in a pilot plant generally using the apparatus shown in the flow chart of the figure accompanying the application. In this example, about 100 pounds of waxy barley (dry basis) containing about 10 wt % moisture were milled through a hammer mill, sifted and the coarse material passed through an Allis Roller Mill until it all passed through a 45 mesh screen. The meal was then rapidly mixed with about 70 pounds of water at about 50° C.

This mixture was immediately centrifuged in a decanter followed by a disc centrifuge to remove residual solids, primarily small start granules. The light phase (liquid) from the disc centrifuge was then immediately heated to about 90° C. in a heat exchanger and again centrifuged to remove coagulated protein. This protein was dried and found to weigh about 3.1 pounds. A chemical analysis thereof indicated the presence of 51 wt % protein and about 6 wt % oil.

The liquid phase from the protein separation was dried on a drum dryer (untrafiltration equipment was not available for this run) and resulted in the production of about 9.9 pounds of beta-glucan solids.

The solids from the initial separation (decanter and disc centrifuge solids) had a wet weight of about 256 pounds and contained about 66 wt % moisture. This indicates a dry weight of about 87 pounds. These solids were mixed with about 92 pounds of additional 50° C. water to make the total solids content of the mixture to be about 25 wt %. This mixture was mixed well and then screened on a 120 mesh screen.

The retained solids were transferred to the syrup line and the material passing through the screen to a starch recovery centrifuge to remove total solids from this stream. These solids are placed in a dough mixer (must be pressed or semi-dried to about 50 wt % solids) and gently agitated until a stiff batter is formed. The dough fork is replaced by a wire agitator, two volumes of warm water added and the mixing continued. The dough quickly disintegrates forming small curds which readily separate on a 170 mesh screen from an almost pure starch stream.

The separated curds are dried producing about 4.9 pounds of vital barley gluten containing about 60 wt % protein. The starch stream is then processed on a disc centrifuge to produce pure starch on an impure light fraction containing small starch granules and some protein which was then transferred to the syrup line. When dried, the starch produced about 24.0 pounds of waxy barley starch.

The residue separated on the 120 mesh screen in the first step of the starch separation and the light phase from the final starch centrifugation were put in the mixing tank, about 0.5 wt % malt and about 15 ml of beta-glucanase were added and the entire contents were heated to about 70° C. while being thoroughly agitated. After reaching about 70° C. and being held for about 5 minutes, the preparation was cooled to about 60° C. and additional 0.5 wt % malt was added and the mixture held for about 12 hours. Shorter times are also adequate. The malt is based on total solids present.

The mixture was then screened on 140 mesh and the retained solids dried producing about 27.9 pounds of sweet barley bran. The material passing through the screen was then centrifuged to remove solids. The solids were then resuspended in water and recentrifuged to wash out sugars and then dried to yield about 5.2 pounds of protein concentrate (about 71 wt % protein). The light phase from the centrifuge (maltose syrup) was heated to about 90° C., treated with decolorizing carbon, filtered, run through an ion-exchange column (Amberlight MB-3), refiltered and evaporated to about 79 wt % solids producing about 31.2 pounds of high maltose syrup.

The invention has been described herein with reference to certain preferred embodiments. However, as obvious variations thereon will become apparent to those skilled in the art, the invention is not to be considered as limited thereto.

We claim:

1. A method for producing and recovering beta-glucan solids, a brain residue, a protein concentrate, a barley oil, waxy barley starch and a maltose syrup from waxy barley, comprising the steps:
   (a) reducing the particle size of waxy barley to form a meal;
   (b) mixing the meal solely with water at a temperature of about 40°-60° C. to produce a liquid water extract and barley solids;
   (c) separating the barley solids from the water extract and heating the water extract at about 80°-115° C.;
   (d) separating coagulated protein from the water extract;
   (e) separating beta-glucan solids containing less than 5.0 wt % protein from water extract remaining after separating coagulated protein in step (d);
   (f) mixing the separated barley solids with water;
   (g) screening off bran to obtain a bran fraction and a liquid passing through the screen;
   (h) separating crude starch by centrifugation from the liquid passing through the screen in step (g);
   (i) kneading the crude starch into a dough, allowing time for dough development and dispersing the dough in water;
   (j) screening the dispersed dough from step (i) to separate barley gluten solids and a liquid dispersion of starch;
   (k) separating waxy barley starch from the dispersion of starch remaining in step (j) by centrifuging the liquid dispersion;
   (l) mixing the bran fraction from step (g) with water, adding an amylolytic enzyme and a beta-glucanase enzyme, and heating to a temperature of about 70°-75° C. for a sufficient period to effect partial starch conversion;
   (m) cooling the mixture to about 50°-60° C.;
   (n) adding an enzyme having at least alpha-amylase activity and maintaining the mixture at this temperature to complete starch conversion and form a liquid starch mixture;
   (o) separating rough solids from the liquid starch mixture and recovering bran residue rough solids and a remaining liquid starch mixture;
   (p) separating solids from the remaining liquid starch mixture of step (o);

(q) extracting the solids with an alcohol to separate a protein concentrate and an extracted barley oil and separately recovering the barley oil and the protein concentrate; and (r) recovering a maltose syrup from liquid remaining after separating solids in step (p).

2. The method of claim 1, further comprising
separating solids from water extract remaining after separating beta-glucan solids in step (e) and recovering undenatured barley gluten from the solids and waxy barley starch substantially free of beta-glucan from water extract remaining after separating the solids.

3. The method of claim 1, wherein
the enzyme added in step (n) comprises alpha-amylase enzyme and beta-amylase enzymes.

4. The method of claim 3, wherein
the enzyme is a green malt enzyme which has both alpha-amylase and beta-amylase activities.

5. The method of claim 1, wherein
the heating in step (c) is conducted for a period of time of about 30 seconds to 10 minutes.

6. The method of claim 1, wherein separating beta-glucan solids in
step (e) is conducted by subjecting the water extract to reverse osmosis to produce a concentrate containing beta-glucans; and
drum drying the concentrate to recover beta-glucan solids.

7. The method of claim 3, wherein
the enzyme is added in step (n) in an amount of about 0.5% by weight of enzyme solids.

8. The method of claim 1, wherein starch conversion in
step (l) is conducted for about 1 to 10 minutes;
cooling in step (m) is to a temperature of about 55°-60° C. to allow added enzymes to further convert starch remaining from step (e); and
the mixture of step (n) is allowed to stand for about 4-8 hours to complete starch conversion.

9. The method of claim 1, further comprising
recovering and recycling the alcohol after recovering the barley oil in step (q) for an additional extraction.

10. The method of claim 1, further comprising
drying the protein concentrate obtained in step (q) to form a protein concentrate containing about 75-80% protein.

11. The method of claim 1, wherein the maltose syrup is recovered from the liquid in step (r) by
decolorizing the liquid with carbon;
filtering off carbon particles and inert materials from the liquid;
deionizing the liquid by ion-exchange; and
evaporating the liquid to produce an about 80 wt % solid maltose syrup.

12. A beta-glucan composition containing less than about 5 wt % protein comprising beta-glucan solids obtained from step (e) in the method of claim 1.

13. A waxy barley starch composition, comprising barley starch substantially free of beta-glucans, protein and oils obtained from step (k) in the method of claim 1.

14. A method for producing and recovering beta-glucan solids, a protein concentrate, waxy barley starch, a barley oil, a maltose syrup, and a bran residue from waxy barley, comprising the steps:

(a) forming a waxy barley meal by reducing the particle size of the barley;

(b) mixing the meal solely with water at a temperature of about 40°-60° C. to form a slurry containing liquid and meal solids;

(c) separating the meals solids from the liquid;

(d) heating the liquid from which meal solids have been separated at a temperature of about 80° to 115° C., centrifuging the liquid to remove coagulated protein, concentrating the liquid from which coagulated protein has been separated by reverse osmosis, and drying the resultant concentrate to produce $\beta$-glucan solids;

(e) mixing the meal solids obtained in step (c) with water at 40°-60° C. to obtain a liquor;

(f) screening off larger particles of barley bran from the liquor;

(g) removing crude starch from the screened liquor by centrifugation;

(h) separating gluten by making a dough from the crude starch removed in step (g), dispersing the dough in water to produce a dispersion, and separating the gluten from the dispersion by screening;

(i) separating waxy barley starch from liquid remaining after screening in step (h) by centrifugation;

(j) mixing the particles of barley bran from step (f) with water at about 40°-60° C. and adding alpha-amylase and beta-glucanase enzymes to form a mixture thereof;

(k) heating the mixture at a temperature of about 70°-75° C. to cause starch liquification and obtain liquified starch;

(l) cooling the liquified starch to about 50°-60° C., adding an additional enzyme preparation comprising alpha-amylase and beta-amylase enzymes to further cause starch conversion and obtain a converted mixture;

(m) subjecting the converted mixture to a rough solids separation to produce a bran residue solid and a liquid product;

(n) separating a solid protein residue from the liquid product from step (m) screening and centrifuging the liquid product, and drying the residue to form a protein concentrate; and (o) recovering a maltose syrup from liquid remaining after separating the protein residue in step (n).

15. The method of claim 14, wherein
step (d) is conducted at a temperature of about 90°-95° C.

16. The method of claim 14, wherein
the enzyme preparation added in step (l) comprises about 0.5 wt % of a green malt containing alpha- and beta-amylase enzymes.

17. The method of claim 14, wherein
the heating in step (k) is conducted for about 1 minute to 10 minutes.

18. The method of claim 14, wherein the
protein concentrate contains about 75-80 wt % protein.

19. The method of claim 14, further comprising recovering the maltose syrup in step (o) by
decolorizing the liquid with carbon;
filtering off the carbon particles and inert materials from the liquid;
deionizing the liquid by ion exchange; and
evaporating the liquid to produce an about 80 wt % solids maltose syrup.

20. The method of claim 14, further comprising
separating solids from liquid remaining after reverse osmosis in step (d);

recovering undenatured barley gluten from the solids; and recovering waxy barley starch substantially free of beta-glucans from liquid remaining after separating solids.

21. The method of claim 14, wherein
the heating in step (d) is conducted for a period of time of about 30 seconds to 10 minutes.

* * * * *